United States Patent
Cesari et al.

(10) Patent No.: US 12,400,425 B2
(45) Date of Patent: Aug. 26, 2025

(54) AUTOMATED THERMAL MATURATION ESTIMATION FROM PALYNOLOGICAL SAMPLE IMAGES

(71) Applicant: SAUDI ARABIAN OIL COMPANY, Dhahran (SA)

(72) Inventors: Christian Andry Cesari, Al Khobar (SA); Mustafa Ali H. Al Ibrahim, Safwa (SA); Mokhles M. Mezghani, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 448 days.

(21) Appl. No.: 17/815,936

(22) Filed: Jul. 28, 2022

(65) Prior Publication Data
US 2024/0037903 A1    Feb. 1, 2024

(51) Int. Cl.
| | |
|---|---|
| *E21B 41/00* | (2006.01) |
| *E21B 43/00* | (2006.01) |
| *E21B 44/00* | (2006.01) |
| *G01N 33/24* | (2006.01) |
| *G06V 10/50* | (2022.01) |
| *G06V 10/75* | (2022.01) |

(52) U.S. Cl.
CPC .......... *G06V 10/758* (2022.01); *E21B 44/00* (2013.01); *G01N 33/24* (2013.01); *G06V 10/507* (2022.01); *E21B 2200/20* (2020.05); *E21B 2200/22* (2020.05)

(58) Field of Classification Search
None
See application file for complete search history.

(56) References Cited

U.S. PATENT DOCUMENTS

| | | |
|---|---|---|
| 4,043,675 A | 8/1977 | Guennel et al. |
| 5,233,409 A | 8/1993 | Schwab |

(Continued)

FOREIGN PATENT DOCUMENTS

| | | | |
|---|---|---|---|
| CN | 108732385 A | 11/2018 | |
| CN | 109408649 | * 3/2019 | ............. G06F 16/51 |
| WO | 2014047709 A1 | 4/2014 | |

OTHER PUBLICATIONS

Karel Zuiderveld; "Contrast Limited Adaptive Histogram Equalization", Graphic Gems; 1994; pp. 474-485 (12 pages).

(Continued)

*Primary Examiner* — Beniyam Menberu
(74) *Attorney, Agent, or Firm* — Osha Bergman Watanabe & Burton LLP

(57) ABSTRACT

A method and a system for estimating a thermal maturity of a rock sample of a subterranean region of interest are disclosed. The method includes preparing a plurality of rock samples of the subterranean region of interest and obtaining an image of an organic matter sample from the plurality of the rock. Further, the histograms are obtained based on RGB pixel values extracted from the image of the organic matter sample and a functional relationship describing the histograms is determined. Additionally, the method includes constructing a regression model using weight values of the functional relationship as input values and estimating the thermal maturity of the rock sample of the subterranean region of interest based on the constructed regression model.

15 Claims, 6 Drawing Sheets

(56) References Cited

U.S. PATENT DOCUMENTS

| | | | |
|---|---|---|---|
| 10,198,804 | B2 | 2/2019 | Sungkorn et al. |
| 2007/0061079 | A1* | 3/2007 | Hu .......................... E21B 25/00 702/6 |
| 2014/0338897 | A1 | 11/2014 | Pomerantz |
| 2016/0320509 | A1* | 11/2016 | Almuhaidib ........... G01V 1/306 |
| 2018/0347354 | A1 | 12/2018 | Li et al. |

OTHER PUBLICATIONS

Akiba et al.; "Optuna: A Next-generation Hyperparameter Optimization Framework", The 25th ACM SIKDD Conference on Knowledge Discovery and Data Mining (KDD '19); Aug. 4, 2019; pp. 2623-2631 (9 pages).

Al-Hajeri et al.; "Maturity estimation for Type II-S kerogen using Raman spectroscopy—A case study from the Najmah and Makhul Formations in Kuwait", International Journal of Coal Geology; vol. 217; 2018 (33 pages).

A. A. Goshtasby and S. Nikolov; "Guest editorial: Image fusion: Advances in the state of the art", Information Fusion; vol. 8, Issue 2; Apr. 2007; pp. 114-118 (5 pages).

R. Bertrand; "Correlations Among The Reflectances Of Vitrinite, Chitinozoans, Graptolites and Scolecodonts", Organic Geochemistry; vol. 15; No. 6; 1990; pp. 565-574 (10 pages).

R. Bertrand and Y. Heroux; "Chitinozoan, Graptolite, and Scolecodont Reflectance As An Alternative to Vitrinite and Pyrobitumen Reflectance in Ordovician and Silurian Strata, Anticosti Island, Quebec, Canada", The American Association of Petroleum Geologists Bulletin; vol. 71; No. 8; Aug. 1987; pp. 951-967 (7 pages).

L. Breiman; "Random Forests", Machine Learning; vol. 45; 2001; pp. 5-32 (28 pages).

T. Chen and C. Guestrin; "XGBoost: A Scalable Tree Boosting System", KDD 16': Proceedings of the 22nd ACM SIGKDD International Conference on Knowledge Discovery and Data Mining, Aug. 2016; pp. 785-794 (10 pages).

S. Cheshire et al.; "Assessing thermal maturity beyond the reaches of vitrinite reflectance and Rock-Eval pyrolysis: A case study from the Silurian Qusaiba formation", International Journal of Coal Geology; vol. 180; Jul. 1, 2017 (64 pages).

G. Clayton et al.; "Correlation of Palynomorph Darkness Index and vitrinite reflectance in a submature Carboniferous well section in northern Saudi Arabia", Revue de micropaleontologie; vol. 60; Issue 3; Jul. 2017 (6 pages).

D. M. Clementz et al.; "Well Site Geochemistry By Programmed Pyrolysis", OTC 3410; Offshore Technology Conference; 1979; pp. 465-470 (6 pages).

Nilanjan Dey; "Uneven illumination correction of digital images: A survey of the state-of-the-art", Optik—International Journal for Light and Electron Optics; vol. 183; 2019; pp. 483-495 (13 pages).

K. Ertug et al.; "Palynofacies, paleoenvironment and thermal maturity of early Silurian shales in Saudi Arabia (Qusaiba Member of Qalibah Foundation)", Review of Palaeobotany and Palynology; vol. 270; 2019; pp. 8-18 (11 pages).

Fan et al.; "Brief review of image denoising techniques", Visual Computing for Industry, Biomedicine, and Art; vol. 2; No. 7; Jul. 8, 2019 (12 pages).

L. H. Gilpin et al.; "Explaining Explanations: An Overview of Interpretability of Machine Learning", 2018 IEEE 5th International Conference on Data Science and Advanced Analytics; 2018; pp. 80-89 (10 pages).

C. R. Harris et al.; "Array programming with NumPy", Nature; vol. 585; Sep. 17, 2020; pp. 357-362 (6 pages).

C. Hartkopf-Fröder et al.; "Optical thermal maturity parameters and organic geochemical alteration at low grade diagenesis to anchimetamorphism: A review", International Journal of Coal Geology; vol. 150-151; Jun. 2015; pp. 74-119 (46 pages).

W. Huang and Z. Jing; "Evaluation of focus measures in multi-focus image fusion", Pattern Recognition Letters; vol. 28; Issue 4; Mar. 1, 2007; pp. 493-500 (8 pages).

J. D. Hunter; "Matplotlib: A 2D Graphics Enviroment", Scientific Programming; Computing in Science & Engineering; vol. 9; Issue 3; Jun. 18, 2007; pp. 90-95 (6 pages).

S. Inan et al.; "The Silurian Qusaiba Hot Shales of Saudi Arabia: An integrated assessment of thermal maturity", International Journal of Coal Geology; vol. 159; Apr. 1, 2016; pp. 107-119 (13 pages).

H. Jacob; "Classification, structure, genesis and practical importance of natural solid oil bitumen", International Journal of Coal Geology; vol. 11; Issue 1; Feb. 1989; pp. 65-79 (15 pages).

D. M. Jarvie et al.; "Oil and Shale Gas from Barnett Shale, Ft. Worth Basin, Texas*", AAPG National Convention, Denver CO; Jun. 2001 (28 pages).

G. Ke et al.; "LightGBM: A highly Efficient Gradient Boosting Decision Tree", Proceedings of the 31st International Conference on Neural Information Processing Systems; 2017; pp. 1-9 (9 pages).

S. Kullback and R. A. Leibler; "On Information and Sufficiency", The Annals of Mathematical Statistics; vol. 22; No. 1; 1951; pp. 79-86 (8 pages).

E. Lafargue et al.; "Rock-Eval 6 Applications in Hydrocarbon Exploration, Production and Soil Contamination Studies", Revue De L'Institut Francais du Petrole; vol. 53; No. 4; 1998 (17 pages).

G. P. Lis et al.; "FTIR absorption indices for thermal maturity in comparison with vitrinite reflectance R0 in type-II kerogens from Devonian black shales", Organic Geochemistry; vol. 36; Issue 11; Nov. 2005; pp. 1533-1552 (20 pages).

J. E. A. Marshall and B. L. Yule; "Spore colour measurement", In: Jones, T.P. & Rowe, N. P.; Fossil Plants and Spores: Modern Techniques; 1999; pp. 165-168 (4 pages).

D. W. Morrow and D. R. Issler; "Calculation of Vitrinite Reflectance from Thermal Histories: A Comparsion of Some Methods", The American Association of Petroleum Geologists Bulletin; vol. 77; No. 4; Apr. 1993; pp. 610-624 (15 pages).

P. K. Mukhopadhyay; "Vitrinite Reflectance as Maturity Parameter: Petrographic and Molecular Characterization and Its Applications to Basin Modeling", Vitrite Reflectance as a Maturity Parameter; ACS Symposium Series; Ch. 1; Nov. 9, 1994; pp. 1-24 (24 pages).

R. J. Norris and J.J.M. Lewis; "The Geological Modeling of Effective Permeability in Complex Heterolithic Facies", SPE 22692; Society of Petroleum Engineers; 1991; pp. 359-374 (16 pages).

K. E. Peters; "Guidelines for Evaluating Petroleum Source Rock using Programmed Pyrolysis", The American Association of Petroleum Geologists Bulletin; vol. 70; No. 3; Mar. 1986; pp. 318-329 (12 pages).

H. I. Petersen et al.; "Reflectance measurements of zooclasts and solid bitumen in Lower Paleozoic shales, southern Scandinavia: Correlation to vitrinite reflectance", International Journal of Coal Geology; vol. 114; Apr. 8, 2013; pp. 1-18 (18 pages).

S. M. Pizer et al.; "Adaptive Histogram Equalization and Its Variations", Computer Vision, Graphics and Image Processing; vol. 39; 1987; pp. 355-368 (14 pages).

L. Prokhorenkova et al.; "CatBoost: unbiased boosting with categorical features", Advances in Neural Information Processing Systems (NeurIPS 2018); vol. 31; 2018; pp. 1-11 (11 pages).

C. L. Riediger, "Solid bitumen reflectance and Rock-Eval Tmax as maturation indices: an example from the 'Nordegg Member', Western Canada Sedimentary Basin", International Journal of Coal Geology; vol. 22; 1993; pp. 295-315 (21 pages).

M. Rocklin; "Dask: Parallel Computation with Blocked algorithms and Task Scheduling", Proc. Of The 14th Python in Science Conf.; 2015; pp. 130-136 (7 pages).

O. Ronneberger et al.; "U-Net: Convolutional Networks for Biomedical Image Segmentation", arXiv:505.04597v1; May 18, 2015; pp. 1-8 (8 pages).

A. Schito et al.; "Comparing optical and Raman spectroscopic investigations of phytoclasts and sporomorphs for thermal maturity assessment: the case study of Hettangian continental facies in the Holy cross Mts. (central Poland)", Marine and Petroleum Geology, vol. 104; Jun. 2019; pp. 331-345 (15 pages).

J. T. Senftle and C. R. Landis; "Vitrinite Reflectance as a Tool To Assess Thermal Maturity", in: Source and migration processes and evaluation techniques; Ch. 12; 1991; pp. 119-125 (7 pages).

(56) References Cited

OTHER PUBLICATIONS

A. Sorci et al.; "Palynomorph optical analyses for thermal maturity assessment of Upper Ordovician (Katian-Hirnantian) rocks from Southern Estonia", Marine and Petroleum Geology; vol. 120; Oct. 2020; pp. 1-15 (15 pages).

A. Spina et al.; "Application of Palynomorph Darkness Index (PDI) to assess the thermal maturity of palynomorphs: A case study from North Africa", International Journal of Coal Geology; vol. 188; Mar. 1, 2018; pp. 64-78 (15 pages).

Frank L. Staplin; "Sedimentary Organic Matter, Organic Metamorphism, and Oil and Gas Occurence", Bulletin of Canadian Petroleum Geology; vol. 17; No. 1; Mar. 1969; pp. 47-66 (20 pages).

J. J. Sweeney and A. K. Burnham; "Evaluation of a Simple Model of Vitrinite Reflectance Based on Chemical Kinetics", The American Association of Petroleum Geologists Bulletin; vol. 74; No. 10; Oct. 1990; pp. 1559-1570 (12 pages).

S. S. Tahoun et al.; "Modified RGB-based kerogen maturation index (KMI): Correlation and calibration with classical thermal maturity indices", International Journal of Coal Geology; vol. 190; Apr. 1, 2018 (14 pages).

R. C. Tobin and B. L. Claxton; "Multidisciplinary thermal maturity studies using vitrinite reflectance and fluid inclusion microthermometry: A new calibration of old techniques", AAPG Bulletin; vol. 84; No. 10; Oct. 2000; pp. 1647-1665 (19 pages).

J. F. Unsworth and H. Gough; "Characterization of coals by automated optical image analysis: 1. Vitrinite reflectance", Journal of Microscopy; vol. 156; No. 3; Dec. 1989; pp. 313-326 (14 pages).

P. Virtanen et al.; "SciPy 1.0: fundamental algorithms for scientific computing in Python", Nature Methods; Perspectives; vol. 17; Feb. 3, 2020; pp. 261-272 (12 pages).

Stéfan van der Walt et al.; "scikit-image: image processing in Python", PeerJ; Jun. 19, 2014; pp. 1-18 (18 pages).

R. W. T. Wilkins et al.; "Should fluorescence alteration replace vitrinite reflectance as a major tool for thermal maturity determination in oil exploration?", Organic Geochemistry; vol. 22; No. 1; 1995; pp. 191-209 (19 pages).

S. Vranjes-Wessely et al.; "High-speed nanoindentation mapping of ogranic matter-rich rocks: A critical evaluation by correlative imaging and machine learning data analysis", International Journal of Coal Geology; vol. 247; Nov. 1, 2021 (52 pages).

Andrew Francis Weller; "The semi-automated classification of sedimentary organic matter and dinoflagellate cysts in balynological preparations", University of Glamorgan/Prifysgol Morgannwg; Sep. 2004 (173 pages).

Makled, Walid A., and Sameh S. Tahoun; "Digital quantification of the miospore coloration to assess the thermal maturity: Novel RGB-based measuring technique"; Marine and Petroleum Geology; vol. 67; El Sevier; May 5, 2015 (15 pages).

Office Action issued in Saudi Arabian Application No. 123450041, mailed on May 3, 2025 (18 pages).

* cited by examiner

AUTOMATED THERMAL MATURATION ESTIMATION FROM PALYNOLOGICAL SAMPLE IMAGES

BACKGROUND

Estimating the state and history of thermal maturity of source rocks is an important part of understanding petroleum systems, and therefore, a successful oil and gas exploration. Using vitrinite reflectance for thermal maturity estimation is a standard in the oil and gas industry. Vitrinite reflectance (% $R_o$) is measured as a percentage of the light reflected from specific particles in the rock called vitrinite. The estimation procedure requires expertise in identifying the vitrinite fragments under an optical microscope and then estimating their reflectance either manually or automatically with the assistance of imaging techniques. Vitrinite reflectance can also be modeled using the thermal history of the kerogen. Related to the observed correlation between thermal history and vitrinite reflectance values, the pyrolysis measurements, specifically the maximum temperature ($T_{max}$), can also be used to estimate thermal maturity. These analyses are also a standard in the oil and gas industry.

Less expensive methods, relying on visual observations of microscopic fossils, especially those of pollen or spores, ("palynomorphs"), have been proposed and used in the past. A number of scales exist for estimating thermal maturity from palynological samples. Example of these methods are Palynomorph Darkness Index (PDI), Spore Color Index (SCI), Thermal Alteration Index (TAI), and Acritarch Alteration Index (AAI). These methods have been evaluated and compared in a number of studies.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments disclosed herein relate to a method of estimating a thermal maturity of a rock sample of a subterranean region of interest. The method includes preparing a plurality of rock samples of the subterranean region of interest and obtaining an image of an organic matter sample from the plurality of the rock. Further, the histograms are obtained based on RGB pixel values extracted from the image of the organic matter sample and a functional relationship describing the histograms is determined. Additionally, the method includes constructing a regression model using weight values of the functional relationship as input values and estimating the thermal maturity of the rock sample of the subterranean region of interest based on the constructed regression model.

In general, in one aspect, embodiments disclosed herein relate to a non-transitory computer readable medium storing a set of instructions executable by a computer processor, the set of instructions including the functionality for obtaining histograms based on RGB pixel values extracted from an image of an organic matter sample and determining a functional relationship describing the histogram. Further, regression model is constructed using weight values of the functional relationship as input values and a thermal maturity of a rock sample of a subterranean region of interest is estimating based on the constructed regression model.

In general, in one aspect, embodiments disclosed herein relate to a system including a drilling system and a thermal maturity simulator comprising a computer processor, the thermal maturity simulator comprising functionality for obtaining histograms based on RGB pixel values extracted from an image of an organic matter sample and determining a functional relationship describing the histograms. Further, thermal maturity simulator comprises functionality for constructing a regression model using weight values of the functional relationship as input values and estimating a thermal maturity of a rock sample of a subterranean region of interest based on the constructed regression model.

Other aspects and advantages of the claimed subject matter will be apparent from the following description and the appended claims.

Other aspects and advantages of the claimed subject matter will be apparent from the following description and the appended claims.

BRIEF DESCRIPTION OF DRAWINGS

Specific embodiments disclosed herein will now be described in detail with reference to the accompanying figures. Like elements in the various figures are denoted by like reference numerals for consistency. Like elements may not be labeled in all figures for the sake of simplicity.

DETAILED DESCRIPTION

Figure 1:
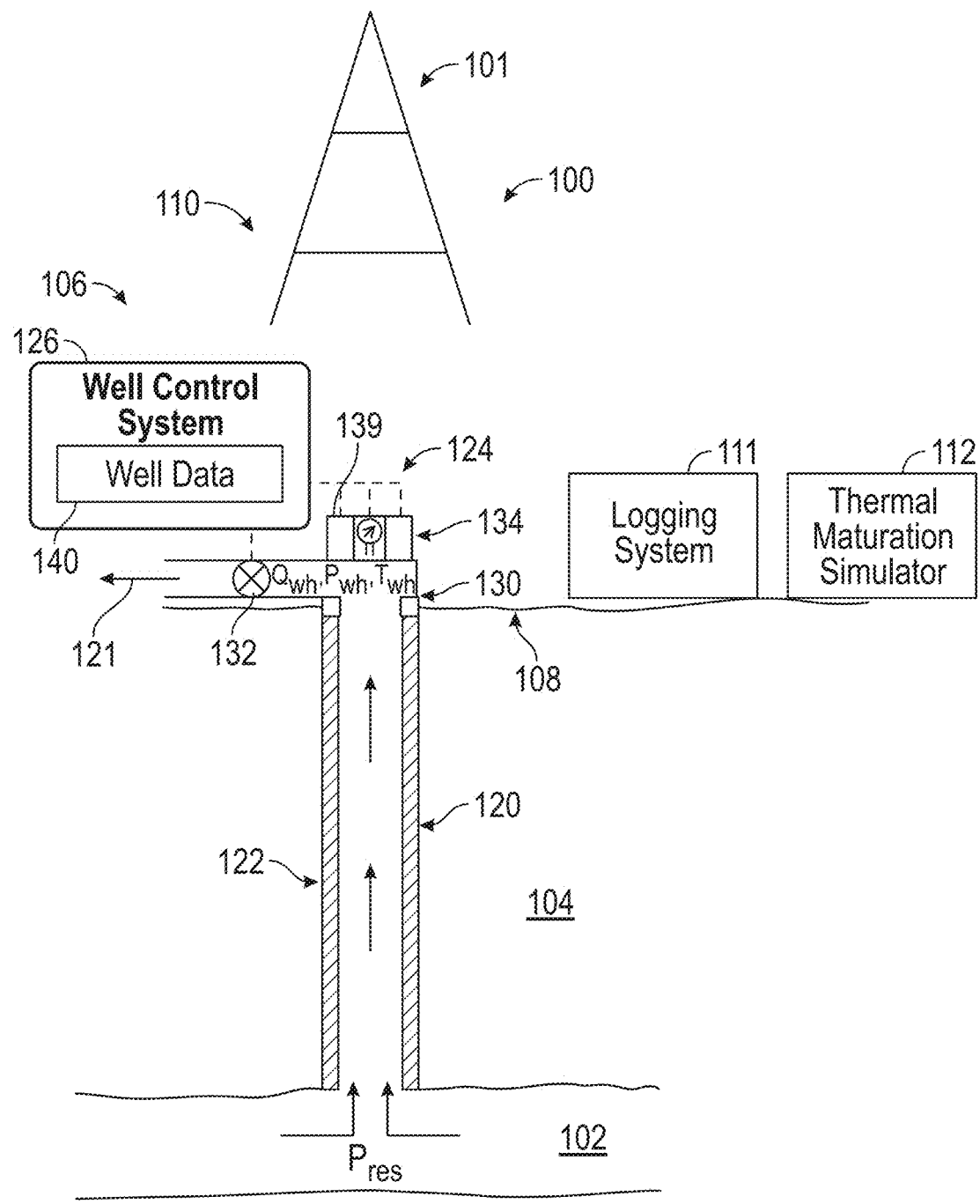
FIG. 1 shows a system in accordance with one or more embodiments.

In the following detailed description of embodiments disclosed herein, numerous specific details are set forth in order to provide a more thorough understanding disclosed herein. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers does not imply or create a particular ordering of the elements or limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-8, any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a rock sample" includes reference to one or more of such rock samples.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope disclosed herein should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

Embodiments disclosed herein provide a method and system for the automated workflow for the estimation of the thermal maturity based on palynological images. The workflow utilizes image processing and machine learning techniques to estimate thermal maturity from the whole sample, automatically aiding experts in the interpretation. The workflow consists of examining the histogram of the pixel values, fitting a mathematical function on the histograms, and fitting a machine learning model to relate the histograms to the thermal maturity. In one or more embodiments, the workflow described herein is able to maximize the utilization of palynological samples and enhance hydrocarbon exploration and production efforts.

Further, estimating the thermal maturity of source rocks is an important step in constructing a comprehensive understanding of petroleum systems, and in return, a successful hydrocarbon exploration and production operation. Traditionally, the estimation is done by an expert by studying vitrinite reflectance or by estimating it from pyrolysis measurements. The workflow disclosed herein represents a low-cost automated improvement over the traditional methodologies for estimating thermal maturity using palynological sample images, such as, at least, PDA, SCI, TAI, and AAI. The workflow utilizes image processing techniques and machine learning to construct a model. First, a dataset of palynological sample images with known thermal maturity is assembled. The organic matter in each image is extracted by thresholding. Red, green, and blue (RGB) histograms are then compiled and fitted with mathematical functions. The weights of the functions fitted are used as an input for a prediction model with thermal maturity being the output.

FIG. 1 shows a schematic diagram in accordance with one or more embodiments. As shown in FIG. 1, a well environment (100) includes a hydrocarbon reservoir ("reservoir") (102) located in a sub surface hydrocarbon-bearing formation ("formation") (104) and a well system (106). The hydrocarbon-bearing formation (104) may include a porous or fractured rock formation that resides underground, beneath a geological surface ("surface") (108). In the case of the well system (106) being a hydrocarbon well, the reservoir (102) may include a portion of the hydrocarbon-bearing formation (104). The hydrocarbon-bearing formation (104) and the reservoir (102) may include different layers of rock having varying characteristics, such as varying degrees of permeability, porosity, capillary pressure, and resistivity. In the case of the well system (106) being operated as a production well, the well system (106) may facilitate the extraction of hydrocarbons (or "production") from the reservoir (102).

In some embodiments, the well system (106) includes a rig (101), a drilling system (110), a logging system (111), a thermal maturity simulator (112), a wellbore (120), a well sub-surface system (122), a well surface system (124), and a well control system ("control system") (126). The drilling system (110) may include a drill string, a drill bit, and a mud circulation system for use in drilling the wellbore (120) into the formation (104). The logging system (111) may include one or more logging tools, for use in generating well logs, based on the sensing system (134), of the formation (104). The well control system (126) may control various operations of the well system (106), such as well production operations, well drilling operation, well completion operations, well maintenance operations, and reservoir monitoring, assessment and development operations. In some embodiments, the well control system (126) includes a computer system that is the same as or similar to that of a computer system (600) described below in FIG. 6 and the accompanying description.

The rig (101) is a combination of equipment used to drill a borehole to form the wellbore (120). Major components of the rig (101) include the drilling fluid tanks, the drilling fluid pumps (e.g., rig mixing pumps), the derrick or mast, the draw works, the rotary table or top drive, the drill string, the power generation equipment and auxiliary equipment.

The wellbore (120) includes a bored hole (i.e., borehole) that extends from the surface (108) into a target zone of the hydrocarbon-bearing formation (104), such as the reservoir (102). An upper end of the wellbore (120), terminating at or near the surface (108), may be referred to as the "up-hole" end of the wellbore (120), and a lower end of the wellbore, terminating in the hydrocarbon-bearing formation (104), may be referred to as the "downhole" end of the wellbore (120). The wellbore (120) may facilitate the circulation of drilling fluids during drilling operations, flow of hydrocarbon production ("production") (121) (e.g., oil and gas) from the reservoir (102) to the surface (108) during production operations, the injection of substances (e.g., water) into the hydrocarbon-bearing formation (104) or the reservoir (102) during injection operations, or the communication of monitoring devices (e.g., logging tools) lowered into the hydrocarbon-bearing formation (104) or the reservoir (102) during monitoring operations (e.g., during in situ logging operations).

In some embodiments, during operation of the well system (106), the well control system (126) collects and records well data (140) for the well system (106). During drilling operation of the well (106), the well data (140) may include mud properties, flow rates, drill volume and penetration rates, formation characteristics, etc. In some embodiments, the well data (140) are recorded in real time, and are available for review or use within seconds, minutes or hours of the condition being sensed (e.g., the measurements are available within 1 hour of the condition being sensed). In such an embodiment, the well data (140) may be referred to as "real-time" well data (140). Real-time well data (140) may enable an operator of the well (106) to assess a relatively current state of the well system (106), and make real-time decisions regarding a development of the well system (106) and the reservoir (102), such as on-demand adjustments in drilling fluid and regulation of production flow from the well.

In some embodiments, the well surface system (124) includes a wellhead (130). The wellhead (130) may include a rigid structure installed at the "up-hole" end of the wellbore (120), at or near where the wellbore (120) terminates at the geological surface (108). The wellhead (130) may include structures for supporting (or "hanging") casing and production tubing extending into the wellbore (120). Production (121) may flow through the wellhead (130), after exiting the wellbore (120) and the well sub-surface system (122), including, for example, the casing and the production tubing. In some embodiments, the well surface system (124) includes flow regulating devices that are operable to control the flow of substances into and out of the wellbore (120). For example, the well surface system (124) may include one or more production valves (132) that are operable to control the flow of production (121). For example, a production valve (132) may be fully opened to enable the unrestricted flow of production (121) from the wellbore (120), the production valve (132) may be partially opened to partially restrict (or "throttle") the flow of production (121) from the wellbore (120), and production valve (132) may be fully closed to fully restrict (or "block") the flow of production (121) from the wellbore (120), and through the well surface system (124).

In some embodiments, the wellhead (130) includes a choke assembly. For example, the choke assembly may include hardware with functionality for opening and closing the fluid flow through pipes in the well system (106). Likewise, the choke assembly may include a pipe manifold that may lower the pressure of fluid traversing the wellhead. As such, the choke assembly may include a set of high-pressure valves and at least two chokes. These chokes may be fixed or adjustable or a mix of both. Redundancy may be provided so that if one choke has to be taken out of service, the flow can be directed through another choke. In some embodiments, pressure valves and chokes are communicatively coupled to the well control system (126). Accordingly, a well control system (126) may obtain wellhead data regarding the choke assembly as well as transmit one or more commands to components within the choke assembly in order to adjust one or more choke assembly parameters.

Keeping with FIG. 1, in some embodiments, the well surface system (124) includes a surface sensing system (134). The surface sensing system (134) may include sensors for sensing characteristics of substances, including production (121), passing through or otherwise located in the well surface system (124). The characteristics may include, for example, pressure, temperature and flow rate of production (121) flowing through the wellhead (130), or other conduits of the well surface system (124), after exiting the wellbore (120). The surface sensing system (134) may also include sensors for sensing characteristics of the rig (101), such as bit depth, hole depth, drilling fluid flow, hook load, rotary speed, etc.

In some embodiments, the well system (106) includes the thermal maturity simulator (112). For example, the thermal maturity (160) may include hardware and/or software with functionality for generating one or more reservoir models regarding the hydrocarbon-bearing formation (104) and/or performing one or more reservoir simulations. For example, the thermal maturity simulator (112) may store images and data regarding palynological samples for performing simulations. A thermal maturity simulator (112) may further, at least, analyze the palynological samples images, obtain grayscale histograms, determine a polynomial function describing the grayscale histogram, construct a regression model, and/or estimate the thermal maturity of the palynological sample based on the constructed regression model. While thermal maturity simulator (112) is shown at a well site, in some embodiments, the thermal maturity simulator (112) is located away from well site. In some embodiments, thermal maturity simulator (112) may include a computer system that is similar to the computer system (800) described below with regard to FIG. 8 and the accompanying description.

Figure 2:
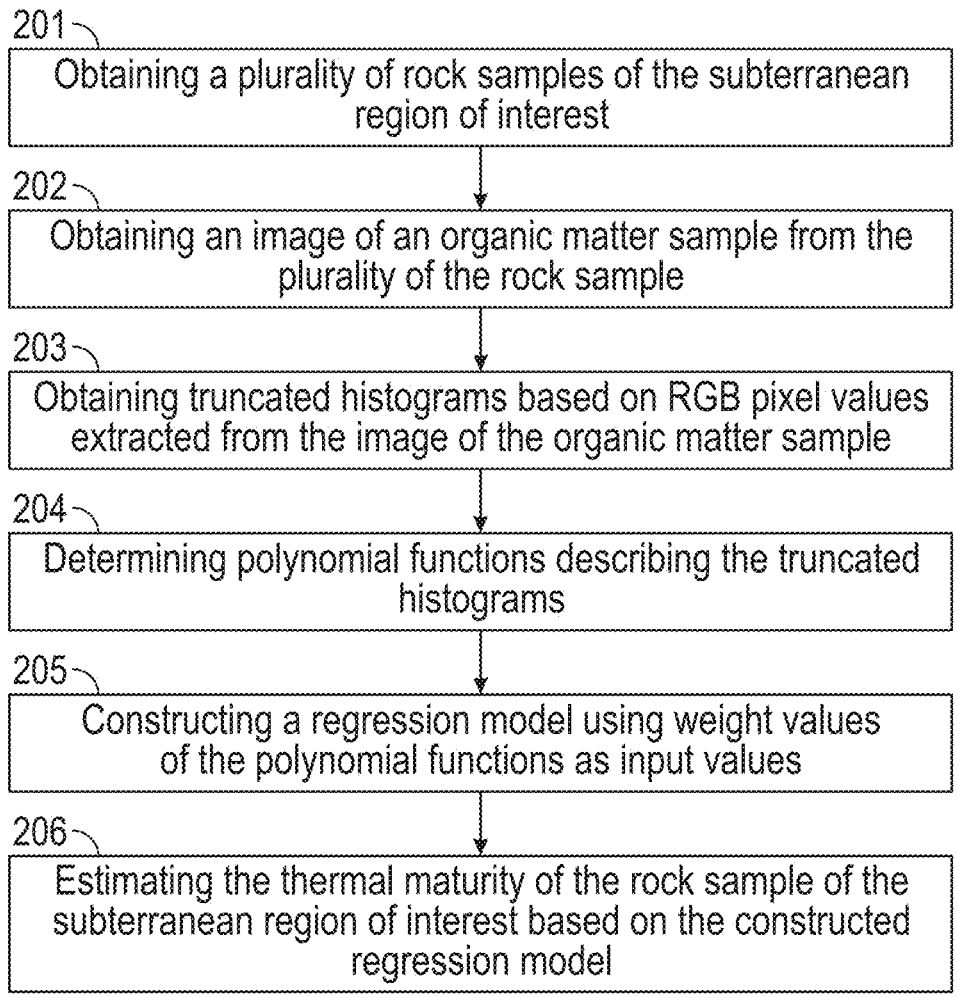
FIG. 2 shows a flowchart in accordance with one or more embodiments.
Figure 3:
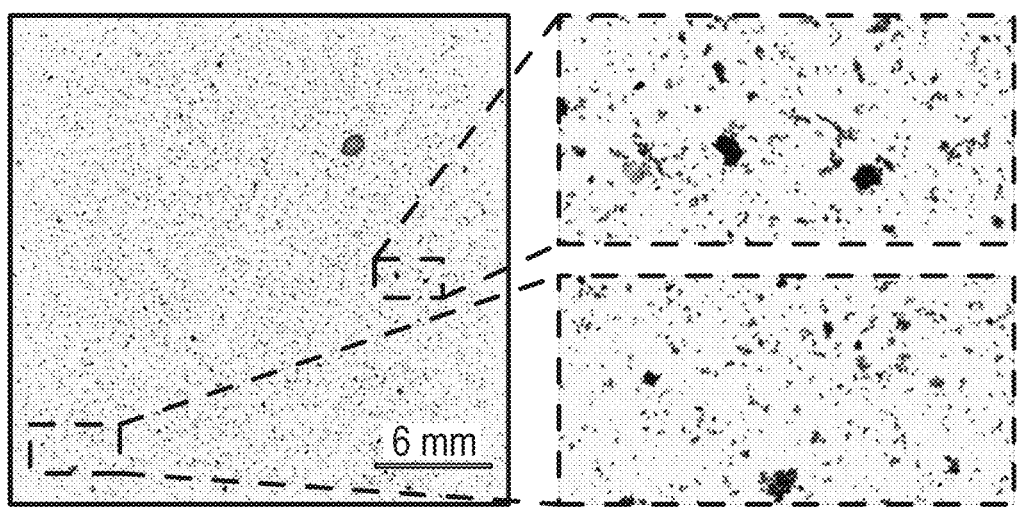
FIG. 3 shows an example of palynomorphs sample image in accordance with one or more embodiments.

FIG. 2 shows a flowchart in accordance with one or more embodiments for estimation of the thermal maturity based on the palynological images. Specifically, in Block 201, a rock samples may be obtained from the subterranean region of interest. In one or more embodiment, the rock sample may originate from a rock core taken from a subterranean region of interest. The core may be conventionally drilled core, or "whole core" collected using a drill bit, having a circular aperture around its rotational axis. In other cases, the rock sample may be taken from a quarry or and outcrop of the rock at the surface. The rock sample may be source rock containing organic matter. The rock samples are initially sieved to remove the large particles from the borehole. The sieves of different aperture sizes may be used in this process, such as the 500 micrometers aperture sieve. After sieving, the filtered rock samples are broken down to smaller particles by mechanical means, such as a mortar and pestle.

After breaking down the rock sample into smaller particles, the rock sample is further chemically processed. Specifically, acids are used to dissolve carbonate components from the rock samples, such as hydrochloric acid (37% concentration), and to dissolve the remaining stronger minerals, such as hydrofluoric acid (50% concentration). To accelerate this acid dissolution, a hotplate can be used to raise the temperature to 100° Celsius. After dissolving all minerals, an organic material is collected into a container. The sample may be further sieved to remove any remaining large particles. Smaller particles are collected in a 10 micrometers meshed sieve and washed with water to remove any residual acid.

The remaining smaller particles are transferred to a small tube with distilled water. A centrifuge may be used for 2 minutes at a 2000 rpm to precipitate the organic matter in the tube. This process allows easy removal of the water by from the tube. Zinc bromide (ZnBr2) solution with density about 1.3 g/cm3 is added to the tube to allow organic particles to float in the solution. The centrifuge may be used on the solution to accelerate the separation process. The organic material is obtained from the top of the solution. To remove the Zinc bromide solution, the 10-micrometer mesh is used again with water to collect the organic material in a clean tube which is then centrifuged at 3000 rpm to precipitate the organic matter and remove excess water.

In accordance with one or more embodiments, in Block 202 at least one image of an organic matter sample is obtained. To obtain the image the obtained organic matter may be transferred to a glass slide. Initially, polyvinyl alcohol (PVA) may be used to separate the organic matter in the test tube and the organic matter transferred to a cover slip using a pipette. The cover slip, containing the organic matter, may be heated using a heating plate to evaporate the liquid PVA. The cover slip may be then attached to a glass slide with, at least, a transparent ultraviolet curing adhesive. The remaining sample is archived in a small, labeled glass vial. The slides may be examined by a palynomorphs expert to estimate the thermal maturity.

The image of the organic matter sample may be obtained using, at least, a thin section scanner, a magnifying objective lens, and a digital camera. The thin section scanner light source and slide may be disposed inside the microscope container to ensure that no light contamination is possible. Automated autofocusing may be used in fixed intervals of time to ensure the best image quality.

In accordance with one or more embodiments, in Block 203 a plurality of histograms may be obtained based on RGB (red, green, blue) pixel values extracted from the image of the organic sample. Initially, the original image may need to be preprocessed, due to the large size of the original image. Preprocessing the image aids processing the analysis in near-real-time manner. In one or more embodiments, the original image may be reduced to obtain a resolution of approximately 1.1 micrometers per pixel. The cropping of the original image may be manual or automated. The automated cropping may be performed using, for example, a machine-learning-based semantic segmentation models, such as U-net, which may detect the sample area automatically. Further, the cropping may be avoided by defining the area to image before the image acquisition time.

Additional preprocessing steps that may be required include correcting uneven illumination from the microscope light source or other light contamination. Further, image fusion algorithms may be used to obtain more focused images when the organic matter present in the sample has variable thickness. Denoising filters, such as a median filter, may be used to reduce the speckle noise in the grainy images. Further, preprocessing may be needed in cases where the dataset is small and multiple sub-images may need to be extracted from each sample. Specifically, the procedure to define the sub-image may be random or uniform, such as dividing each image to a predetermined number of separate blocks, where each block covers a representative area of the sample. The representative area for the sample may be defined using the representative area analysis, which analyzes the heterogeneity in the sample. Further, the sample area may be defined based on the similarity of red, green, and blue histograms in the sub-images according to the KL-Divergence.

In accordance with one or more embodiments, after preprocessing the original image, the red ($p_{red}$), green ($p_{green}$), and blue ($p_{blue}$) pixel values may be converted to grayscale ($p_{gray}$). For example, $p_{gray}$ may be calculated as:

$$p_{gray} = 0.2125 p_{Red} + 0.7154 p_{Green} + 0.0721 p_{Blue} \quad \text{Equation (1)}$$

Figures 4A, 4B:
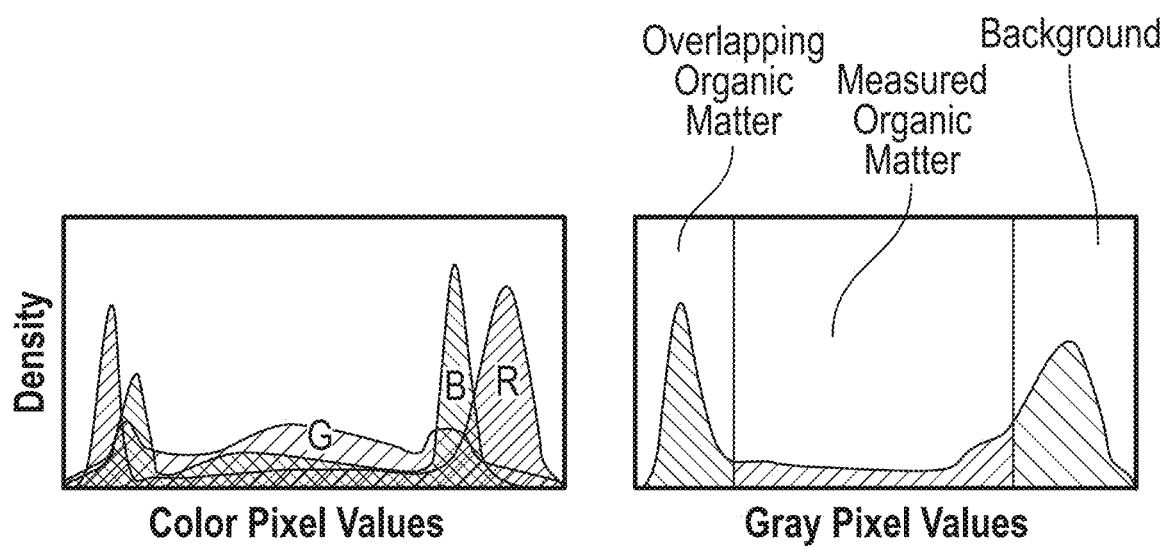
FIGS. 4A and 4B show RGB and gray histograms in accordance with one or more embodiments.

As shown, FIG. 4A represents the color pixel values on x-axis and the density of each color pixel value on y-axis. The density a color pixel value represents a number of the color pixel values in the image. Further, density of the color pixel values is determined for red, blue and green pixel values are represented as a histogram.

In one or more embodiments, the Equation (1) is used to convert the red, green, and blue color pixel values into the grayscale, which is shown on FIG. 4B which represents the gray pixel values on x-axis and the density of each gray pixel value on y-axis. Specifically, in FIG. 4B, after calculating the grayscale values, the pixels with extreme values, white pixels with low values and black pixels with high values, are removed. High values of pixels constitute the background of the sample which may occupy more than 70% of the image. Additionally, low values commonly relate to overlapping organic matter, representing layers of the organic matter blocking the light source, which prevents the sample to reflect the thermal maturity.

Alternatively, the process of cutting of the high and low pixel values may be automated by automatically identifying local maximum in the histogram. The process of automated cutoff may be especially useful in cases where there is variability in the acquisition parameters, such as the lighting intensity. For exemplary purposes, for identifying the overlapping organic matter cutoff, the local maximum at the first 20% of the gray histogram pixel values may be identified. Further, the cutoff is set to be 10% higher than the local maximum. Similar procedure may be done for setting the cutoff for the background. The local maximum at the last 20% of the gray histogram pixel values is identified. Further, the cutoff is set to be 10% lower than the local maximum. The truncated histogram may be normalized and scaled so that the resulting values lie in the range between 0 and 255.

In one or more embodiments, the cutoffs may be determined automatically or manually in the grayscale histogram. The pixels that are removed in the cutoff process of the grayscale histogram are also removed from the original RGB image. In this process, pixels from the original RGB image are filtered and the new RGB image is comprised only of filtered subsets of pixels. Thus, the original RGB image may be filtered based on kept pixels in the grayscale histograms (i.e., where only a subset of the pixels in the image are kept). Pixels from the filtered RGB image are used to construct truncated RGB histograms, based on subsets of filtered pixels.

Alternatively, in one or more embodiments the cutoffs may be determined manually on the original RGB image, based on the expert's analysis. In such embodiments, the original RGB image pixels may not be transformed to the grayscale pixel values to perform the cutoff process. The RGB histogram is determined based on the filtered RGB pixels.

Continuing with FIG. 2, Block 204 determines a polynomial function describing the histograms (either grayscale or non-grayscale based on the methods described above with respect to Step 204). The stretched truncated histogram data may be fitted to a function using Equation 2.

$$F(p) = a_n p^n + a_{n-1} p^{n-1} + a_{n-2} p^{n-2} + \ldots + a_1 p + a_0 \quad \text{Equation (2)}$$

Equation 2 defines the equation for polynomial function, $F(p)$, of degree n where p is the pixel value and a constants are the weights. However, the stretched truncated histogram data may be fitted to a function using alternative methods and equations. The weights for the fitted function are used to represent the image. For example, given an image that is converted to the histogram, the histogram may be fitted to a fourth degree polynomial with a 5 number array constituting the weights of the polynomial. This array is used as the input for a machine learning model in the next step, where the output is assigned as the thermal maturity of the sample. The histograms used for determining a polynomial function may be, at least, the truncated grayscale histogram or the truncated RGB histograms.

Continuing with FIG. 2, Block 205 constructs the regression model using weigh values of the polynomial function from Block 204. Specifically, the regression model is fitted on the data extracted from Block 204 with input being the weights of the fitted function on the histograms and the output being the thermal maturity. A plurality of regression models may be used to estimate the thermal maturity. A specific regression model may be determined, at least, based on the type of data, the size of the data, and/or the variability of data. Further, the complexity of the model also may be a factor in determining a regression model to use. Potential regression models may include, for example, the random forest regression or the gradient regression tree, such as XGBoost, LightGBM, and CatBoost regression trees.

Further, to improve the efficiency of the model, the dataset may be divided into training and test subsets to ensure that the regression model is not overfitting the data, to test the model type and the hyperparameters of the model. Additionally, if the number of samples used is small and insufficient, leave-one-out cross validation (LOOV) may be used to estimate the potential accuracy of the model.

In one or more embodiments, different metrics such as, at least, mean squared error (MSE), root mean squared error, coefficient determination, adjusted coefficient of determination, and mean absolute error may be utilized to optimize the process. Specifically, the mean squared error allows the penalization of large differences more than small differences in the fitting process. Further, using mean absolute error means that the penalization is linearly proportional to the difference between the predict value and the true value. MSE is minimized to fit the models as defined in Equation 3:

$$MSE = \frac{1}{n}\sum_{i=1}^{n}(m_i - \hat{m}_i)^2 \qquad \text{Equation (3)}$$

where $m_i$ is the expert estimated thermal maturity and $\hat{m}_i$ is the model predicted thermal maturity for image i. Additionally, custom functions with variable weights can be used to bias the model to fit certain range of thermal maturity, such as penalizing discrepancies between the fitted and estimated values more at certain thermal maturity range.

Figure 5:
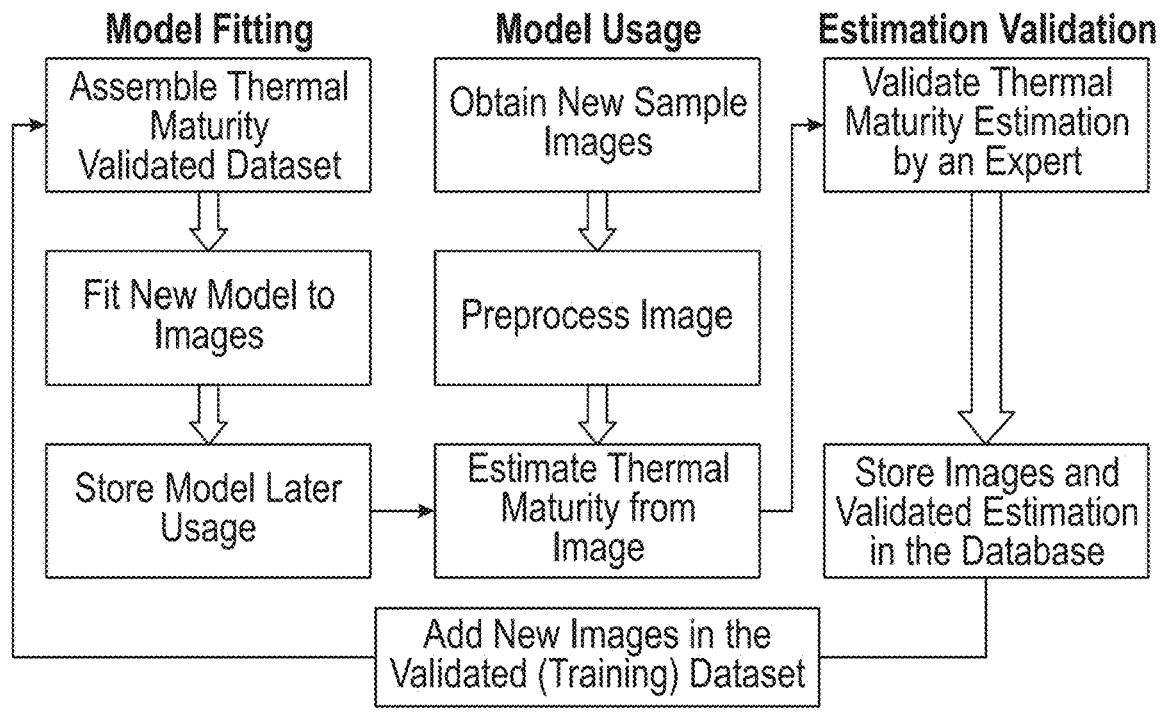
FIG. 5 shows a continuous thermal maturity estimation workflow in accordance with one or more embodiments.

In Block 206, the thermal maturity of the rock sample of the subterranean region of interest is estimated based on the constructed regression model from Block 205. The fully automated workflow may be incorporated into a system that automatically analyzes images after obtaining and storing them as shown on FIG. 5. Specifically, the FIG. 5 shows a continuous process where estimated thermal maturity values are validated or corrected by experts and the samples with relevant values are incorporated into the training dataset. That results with creating a new, robust, fitted, and more accurate model.

The estimated thermal maturity of the sample rock may be used to determine and drill a wellbore path. The wellbore path may be determined to penetrate a hydrocarbon reservoir, for the purpose of characterizing the hydrocarbon reservoir, or for producing hydrocarbons, or both. Additionally, the estimated thermal maturity allows for identification of the content of a reservoir. Identifying the content of a reservoir is crucial for prospect generation during exploration, effective well placement and geosteering in developmental projects as well as reservoir characterization.

Figure 6:
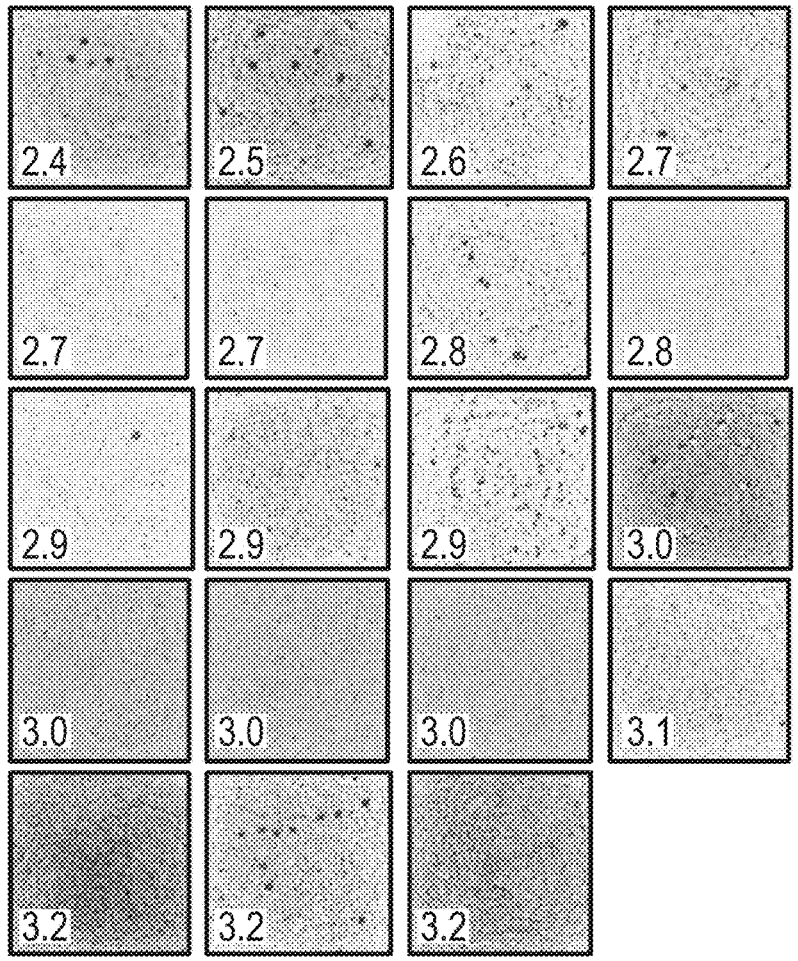
FIG. 6 shows a dataset of palynological samples in accordance with one or more embodiments.

FIG. 6 shows an example of 19 rock samples used to better illustrate the workflow for estimating the thermal maturity of the rock samples. The thermal maturity of each sample was previously estimated based on simultaneous color examinations following the Integrated Palynomorph-Amorphous Organic Matter methodology. The estimates of the thermal maturity are given on a modified TAI scale from 0 to 5, where 0 describes lowest maturity and 5 describes highest maturity. The estimated thermal maturity of 19 samples is in the range from 2.4 to 3.2.

Figures 7A, 7B, 7C:
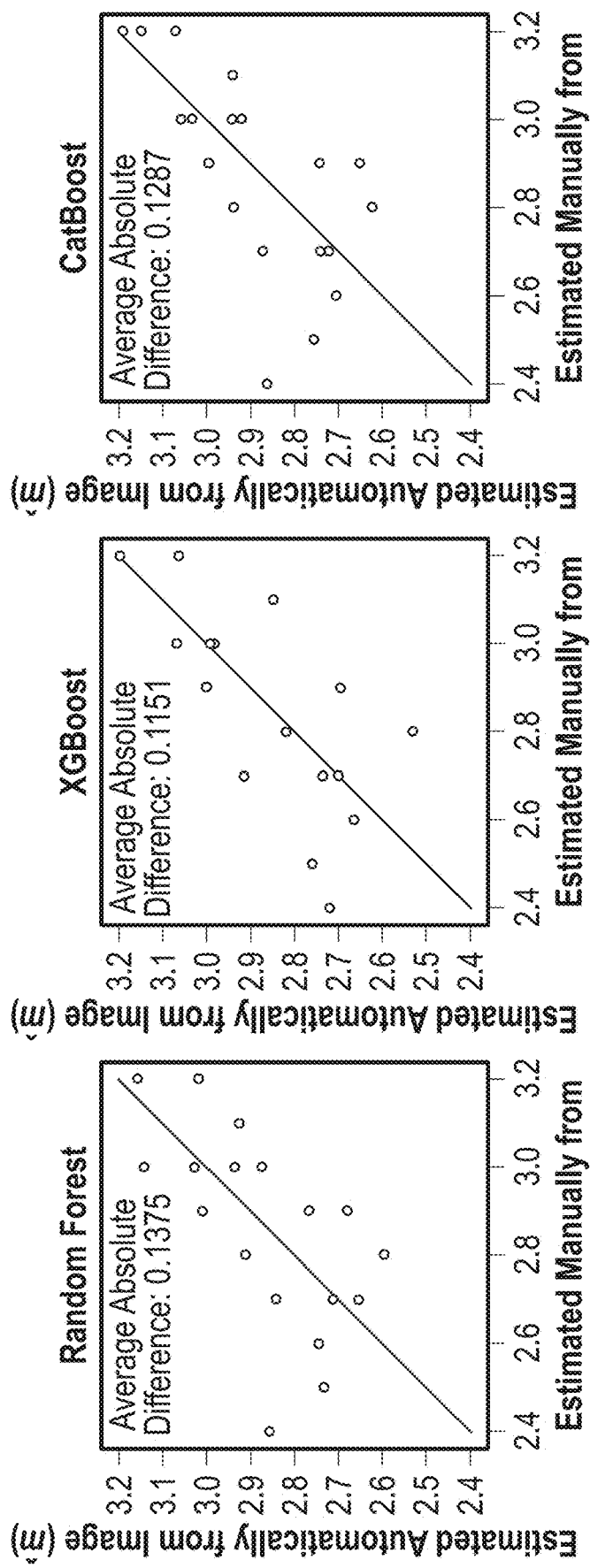
FIGS. 7A, 7B, and 7C show thermal maturity estimation comparison between the automated workflow and the expert's estimation in accordance with one or more embodiments.

Further, FIGS. 7A-7B show the results of fitting a number of regressions models on the dataset. Leave-one-out cross validation is used on each model to estimate the error. The x-axis represents the estimated thermal maturity obtained from the manual observations of experts. The y-axis represents the estimated thermal maturity obtained automatically using one of the machine learning models. Specifically, FIG. 7A shows the thermal maturity determined using the random forest model, with the absolute difference, between manual and automatic estimations, of 0.1375. Further, FIG. 7B shows the thermal maturity determined using the XGBoost model, with the absolute difference, between manual and automatic estimations, of 0.1151. Additionally, FIG. 7C shows the thermal maturity determined using the CatBoost model, with the absolute difference, between manual and automatic estimations, of 0.1287. The lowest average mismatch between the expert's estimation and the automated model estimation is around 0.1151 for XGBoost. Further, the sample with the lowest estimated thermal maturity has the highest discrepancy around 0.3. This is caused by performing the leave-one-out-cross validation, where the sample that is tested is excluded from model fitting. This means that the model used in the estimation of this low thermal maturity sample of 2.4 was fitted with data with minimum thermal maturity of 2.5. Because of this, the model was not expected to perform adequately due to the extrapolation. To remedy this issue, a bigger dataset may be used. Alternatively, data augmentation, such as subsampling of images, can be performed.

Figure 8:
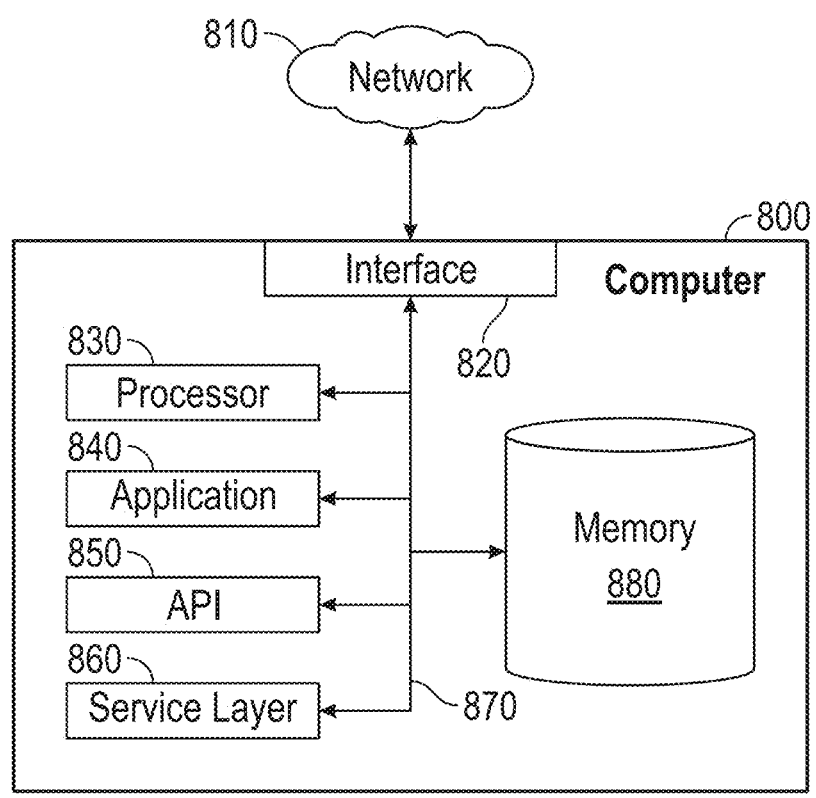
FIG. 8 shows a computer system in accordance with one or more embodiments.

Embodiments may be implemented on any suitable computing device, such as the computer system shown in FIG. 8. Specifically, FIG. 8 is a block diagram of a computer system (800) used to provide computational functionalities associated with described algorithms, methods, functions, processes, flows, and procedures as described in the instant disclosure, according to an implementation. The illustrated computer (800) is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (800) may include a computer that includes an input device, such as a keypad, keyboard, touch screen, or other device that can accept user information, and an output device that conveys information associated with the operation of the computer (800), including digital data, visual, or audio information (or a combination of information), or a GUI.

The computer (800) can serve in a role as a client, network component, a server, a database or other persistency, or any other component (or a combination of roles) of a computer system for performing the subject matter described in the instant disclosure. The illustrated computer (800) is communicably coupled with a network (810). In some implementations, one or more components of the computer (800)

may be configured to operate within environments, including cloud-computing-based, local, global, or other environment (or a combination of environments).

At a high level, the computer (800) is an electronic computing device operable to receive, transmit, process, store, or manage data and information associated with the described subject matter. According to some implementations, the computer (800) may also include or be communicably coupled with an application server, e-mail server, web server, caching server, streaming data server, business intelligence (BI) server, or other server (or a combination of servers).

The computer (800) can receive requests over network (810) from a client application (for example, executing on another computer (800) and responding to the received requests by processing the said requests in an appropriate software application. In addition, requests may also be sent to the computer (800) from internal users (for example, from a command console or by other appropriate access method), external or third-parties, other automated applications, as well as any other appropriate entities, individuals, systems, or computers.

Each of the components of the computer (800) can communicate using a system bus (870). In some implementations, any or all of the components of the computer (800), both hardware or software (or a combination of hardware and software), may interface with each other or the interface (820) (or a combination of both) over the system bus (870) using an application programming interface (API) (850) or a service layer (860) (or a combination of the API (850) and service layer (860). The API (850) may include specifications for routines, data structures, and object classes. The API (850) may be either computer-language independent or dependent and refer to a complete interface, a single function, or even a set of APIs. The service layer (860) provides software services to the computer (800) or other components (whether or not illustrated) that are communicably coupled to the computer (800). The functionality of the computer (800) may be accessible for all service consumers using this service layer. Software services, such as those provided by the service layer (860), provide reusable, defined business functionalities through a defined interface. For example, the interface may be software written in JAVA, C++, or other suitable language providing data in extensible markup language (XML) format or other suitable format. While illustrated as an integrated component of the computer (800), alternative implementations may illustrate the API (850) or the service layer (860) as stand-alone components in relation to other components of the computer (800) or other components (whether or not illustrated) that are communicably coupled to the computer (800). Moreover, any or all parts of the API (850) or the service layer (860) may be implemented as child or sub-modules of another software module, enterprise application, or hardware module without departing from the scope of this disclosure.

The computer (800) includes an interface (820). Although illustrated as a single interface (820) in FIG. 8, two or more interfaces (820) may be used according to particular needs, desires, or particular implementations of the computer (800). The interface (820) is used by the computer (800) for communicating with other systems in a distributed environment that are connected to the network (810). Generally, the interface (820 includes logic encoded in software or hardware (or a combination of software and hardware) and operable to communicate with the network (810). More specifically, the interface (820) may include software supporting one or more communication protocols associated with communications such that the network (810) or interface's hardware is operable to communicate physical signals within and outside of the illustrated computer (800).

The computer (800) includes at least one computer processor (830). Although illustrated as a single computer processor (830) in FIG. 8, two or more processors may be used according to particular needs, desires, or particular implementations of the computer (800). Generally, the computer processor (830) executes instructions and manipulates data to perform the operations of the computer (800) and any algorithms, methods, functions, processes, flows, and procedures as described in the instant disclosure.

The computer (800) also includes a memory (880) that holds data for the computer (800) or other components (or a combination of both) that can be connected to the network (810). For example, memory (880) can be a database storing data consistent with this disclosure. Although illustrated as a single memory (880) in FIG. 8, two or more memories may be used according to particular needs, desires, or particular implementations of the computer (800) and the described functionality. While memory (880) is illustrated as an integral component of the computer (800), in alternative implementations, memory (880) can be external to the computer (800).

The application (840) is an algorithmic software engine providing functionality according to particular needs, desires, or particular implementations of the computer (800), particularly with respect to functionality described in this disclosure. For example, application (840) can serve as one or more components, modules, applications, etc. Further, although illustrated as a single application (840), the application (840) may be implemented as multiple applications (840) on the computer (800). In addition, although illustrated as integral to the computer (800), in alternative implementations, the application (840) can be external to the computer (800).

There may be any number of computers (800) associated with, or external to, a computer system containing computer (800), each computer (800) communicating over network (810). Further, the term "client," "user," and other appropriate terminology may be used interchangeably as appropriate without departing from the scope of this disclosure. Moreover, this disclosure contemplates that many users may use one computer (800), or that one user may use multiple computers (800).

In some embodiments, the computer (800) is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (SaaS), mobile "backend" as a service (MBaaS), serverless computing, artificial intelligence (AI) as a service (AIaaS), and/or function as a service (FaaS).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. A method of estimating a thermal maturity of a rock sample of a subterranean region of interest, comprising:
preparing a plurality of rock samples of the subterranean region of interest;
obtaining an image of an organic matter sample from the plurality of the rock samples using a thin section scanner, an objective lens, and an image recording device;
obtaining, using a computer processor, histograms based on RGB pixel values extracted from the image of the organic matter sample;
determining, using the computer processor, a functional relationship describing the histograms;
constructing, using the computer processor, a regression model using weight values of the functional relationship as input values;
estimating, using the computer processor, the thermal maturity of the rock sample of the subterranean region of interest based on the constructed regression model;
determining content of the subterranean region of interest based on the thermal maturity of the rock sample;
determining a wellbore path based on the thermal maturity of the rock and the identified content of the subterranean region of interest; and
drilling a wellbore using a drilling system guided by the determined wellbore path.

2. The method of claim 1, wherein the RGB pixels are converted to grayscale pixel values,
wherein grayscale histograms are constructed using the grayscale pixel values, and
wherein the grayscale histograms are filtered to remove the grayscale pixels with high and low values.

3. The method of claim 1, further comprising: converting the RGB pixels to grayscale pixel values,
wherein the grayscale pixel values are filtered to remove the grayscale pixels with high and low values, and
wherein RGB histograms are constructed using the filtered grayscale pixel values.

4. The method of claim 1, wherein preparing the organic matter sample from the plurality of rock samples comprises:
sieving the plurality of rock samples;
breaking the sieved plurality of rock samples into smaller pieces;
removing an organic material from the broken plurality of rock samples using a plurality of acids;
isolating the organic material using centrifuge; and
transferring the organic material to a glass slide.

5. The method of claim 1, wherein the plurality of the rock sample comprise processed palynological samples.

6. The method of claim 1, wherein the functional relationship comprises a polynomial function.

7. The method of claim 1, wherein a machine learning semantic segmentation model is used to detect a portion of the image with a largest amount of the organic matter.

8. The method of claim 1, wherein the RGB pixels with lowest and highest values are ignored, and wherein cutoffs for the lowest and the highest values are identified based on a local maximum of the histograms.

9. The method of claim 1, wherein multiple metrics are used in optimization process, the multiple metrics including a mean squared error, a root mean squared error, a coefficient of determination, an adjusted coefficient of determination, and a mean absolute error.

10. A non-transitory computer readable medium storing instructions executable by a computer processor, the instructions comprising functionality for:
obtaining histograms based on RGB pixel values extracted from an image of an organic matter sample;
determining a functional relationship describing the histogram;
constructing a regression model using weight values of the functional relationship as input values;
estimating a thermal maturity of a rock sample of a subterranean region of interest based on the constructed regression model;
determining content of the subterranean region of interest based on the thermal maturity of the rock sample; and
determining a wellbore path based on the thermal maturity of the rock and the identified content of the subterranean region of interest,
wherein a wellbore is drilled using a drilling system guided by the determined wellbore path.

11. The non-transitory computer readable medium of claim 10, wherein a plurality of the rock sample is processed palynological samples.

12. The non-transitory computer readable medium of claim 10, wherein a machine learning semantic segmentation model is used to detect a portion of the image with a largest amount of the organic matter.

13. The non-transitory computer readable medium of claim 10, wherein the RGB pixels with lowest and highest values are ignored, and wherein cutoffs for the lowest and the highest values are identified based on a local maximum of the histograms.

14. A system comprising:
a thermal maturity simulator comprising a computer processor, the thermal maturity simulator comprising functionality for:
obtaining histograms based on RGB pixel values extracted from an image of an organic matter sample;
determining a functional relationship describing the histograms;
constructing a regression model using weight values of the functional relationship as input values; and
estimating a thermal maturity of a rock sample of a subterranean region of interest based on the constructed regression model;
determining content of the subterranean region of interest based on the thermal maturity of the rock sample; and
determining a wellbore path based on the thermal maturity of the rock and the identified content of the subterranean region of interest; and
a drilling system, configured to drill a wellbore guided by the determined wellbore path.

15. The system of claim 14, wherein the simulator further comprises a functionality for detecting a portion of the image with a largest amount of the organic matter using a machine learning semantic segmentation model.

* * * * *